United States Patent [19]

Kamohara et al.

[11] Patent Number: 4,604,142

[45] Date of Patent: Aug. 5, 1986

[54] INVESTMENTS FOR DENTAL CASTING

[75] Inventors: Hiroshi Kamohara; Shohei Hayashi, both of Tokyo; Nobukazu Ohi, Fuchu, all of Japan

[73] Assignee: G-C Dental Industrial Corp., Tokyo, Japan

[21] Appl. No.: 743,159

[22] Filed: Jun. 10, 1985

[30] Foreign Application Priority Data

Jul. 6, 1984 [JP] Japan ................................ 59-138942

[51] Int. Cl.$^4$ ................................................ B22C 1/08
[52] U.S. Cl. .................................. 106/38.51; 164/520; 164/528; 164/516; 164/518; 106/114; 106/35
[58] Field of Search ................ 164/520, 522, 525–529, 164/516–519; 106/38.23, 38.51, 35, 214, 114

[56] References Cited

FOREIGN PATENT DOCUMENTS 738981   3/1970  Belgium ............................. 164/525
 56163   7/1982  European Pat. Off. ............ 164/529
57-184549 11/1982 Japan .................................. 164/522

Primary Examiner—Kuang Y. Lin
Attorney, Agent, or Firm—Oblon, Fisher, Spivak, McClelland & Maier

[57] ABSTRACT

An investment material for dental casting comprises 100 parts by weight of a mixture of hemihydrate gypsum, quartz and/or cristobalite and 2 to 5 parts by weight of natural starch optionally with 0.1 to 1.0 part by weight of soluble starch.

2 Claims, 1 Drawing Figure

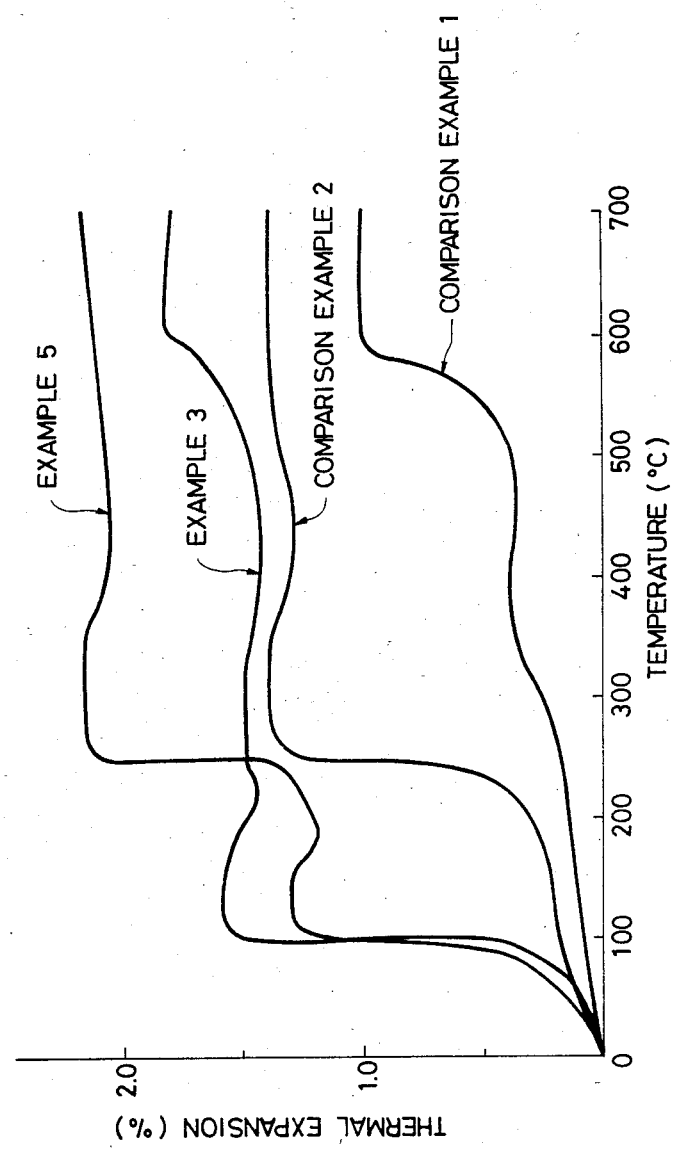

INVESTMENTS FOR DENTAL CASTING

FIELD OF THE INVENTION

The present invention relates to an investment material for dental casting, which is used in the casting of dental alloys.

BACKGROUND OF THE INVENTION

Most crown prosthetic appliance formed of metals are produced by the lost wax process with high casting accuracy.

The investment material to be used for casting is required to possess the following properties:
(1) It has sufficient heat resistance.
(2) It expands so uniformly that the shrinkage on casting of a metal can be made up for.
(3) It has good reproducibility of the surface state of a wax pattern serving as a prototype.
(4) It has good air permeability.
(5) It shows favorable mold release characteristics with respect to cast products without undergoing any baking or chemical reaction.
(6) It has good flowability in a slurried state (before setting).

Currently, use is mainly made of investment materials in which quartz or cristobalite is used as the refractory material. However, it is hard to say that such investment materials sufficiently possess the aforesaid required properties. Many type of alloys for example gold alloy, silver alloy, gold-silver-palladium alloy, silver-palladium alloy, palladium alloy, nickel-chromium alloy, cobalt-chromium alloy, etc., are primarily used as the metals for dental casting. When such alloys are cast in a casting mold, however, there arises shrinkage on casting, or a decrease in volume, which is caused by thermal shrinkage of a melt, a volume change on solidification, thermal shrinkage taking place during cooling to room temperature following solidification, so that the resulting cast product is smaller in size than the prototype. In order to obtain the cast product of the same size as the prototype, it is thus required to give an investment a coefficient of expansion corresponding to the degree of shrinkage on casting of an alloy, thereby to expand the casting mold. The means for expansion of the casting mold to this end now include a combination of the thermal expansion of investments with the setting expansion (esp. the hygroscopic expansion) thereof.

Referring first to thermal expansion, quartz and cristobalite show thermal expansion due to phase transformation at 500°–600° C. and 200°–300° C., respectively. However, such thermal expansion is insufficient to make up for the shrinkage on casting of a metal. For that reason, the setting expansion (esp. the hygroscopic expansion) is further used to expand the investment. However, the setting expansion (esp. the hygroscopic expansion) of the investment becomes partly uneven, so that the wax pattern may possibly deform, thus offering an accuracy problem.

In order to improve the reproducibility of the surface state of the wax pattern, it is required to finely divide refractory particles. However, this is accompanied by a decrease in the air permeability of the investment, thus leading to the incidence of casting deficiencies such as misrum, or resulting in a decrease in the flowability of the investment in a slurried state, which, in turn, results in deterioration of workability during the investing of wax patterns. It is thus impossible to pulverize such particles to no more than any specific particle size.

SUMMARY OF THE INVENTION

To reduce or eliminate the disadvantages of the prior art, studies have been made with a view to preparing an investment material without recourse to the setting expansion (esp. the hygroscopic expansion) showing uneven expansion and leading to the possibility that the wax pattern may deform, said investment material showing expansion enough to make up for the shrinkage on casting of a metal only by thermal expansion showing uniform expansion, and suffering neither decrease in the air permeability, even when the particles of the refractory material are finely divided, nor lowering of the flowability in a slurried state. In consequence, an investment material has been found to be effective, in which natural starch or a combination of natural starch and soluble starch is added to a mixture of hemihydrate gypsum, quartz and/or cristobalite.

According to the present invention, there is provided an investment material for dental casting, in which 2 to 5 parts by weight of natural starch, optionally with 0.1 to 1.0 part by weight of soluble starch are added to 100 parts by weight of a mixture of hemihydrate gypsum, quartz and/or cristobalite.

BRIEF DESCRIPTION OF THE DRAWING

FIG. 1 shows the variations of thermal expansion as function of temperature for different composition.

PREFERRED EMBODIMENTS OF THE INVENTION

The natural starch added to the investment material according to the present invention has its grain expanded at 75° to 110° C., and functions to expand the investment material in that temperature zone. More exactly, the addition of natural starch in a specified amount range assures uniform expansion by way of thermal expansion attributable to the expansion of natural starch grain, which is one of the important properties required for investment materials. As a result, the expansion of the investment material required to make up for the shrinkage on casting of a metal can be obtained by way of a combination of the thermal expansion caused by the expansion of natural starch grain with the thermal expansion caused by the phase transformation of quartz and/or cristobalite without recourse to the setting expansion (esp. hygroscopic expansion). Thus, the investment material according to the present invention undergoes uniform expansion, one of the properties inevitable to the investment material, without causing deformation of the wax pattern. On the other hand, when the wax is incinerated, and the investment material is heated to about 650°–700° C. that are ring temperatures in casting, the natural starch is completely burned out. As a result, very minute voids are formed in the regions of the investment material, which are occupied by the natural starch, and serve to improve the air permeability thereof. This makes it possible to finely divide the particles of the refractory material, so that the proportion of refractory particles present on the surface of the wax pattern increases with improvements in the heat resistance of the investment material as a result. Furthermore, since the thermal expansion can be varied depending upon the amount of natural starch, the investment material of the present invention can be used to cast the high-melting point type dental casting alloy which show large shrinkage on casting such as nickel-chromium base alloys, not to speak of noble metal base alloys and semi-noble metal base alloys.

As mentioned in the foregoing, it is possible to obtain the end properties with respect to expansion and air permeability by mere addition of natural starch to a mixture comprising hemihydrate gypsum, quartz and/or cristobalite. However, further addition of a small amount of soluble starch improves the "wettability" of the investment material slurry with respect to the wax pattern, and functions to divide the crystals of hemihydrate gypsum growing at the contact portion of the wax pattern with the investment material. Thus, the reproducibility of the surface state of the wax pattern is improved, unless the refractory particles are otherwise finely divided. As a result, the cast product is more smooth on the surface, while the flowability of the investment material in a slurried state is improved, with improvements in workability during investing. Furthermore, it is possible to reduce the amount of water to be mixed with powder of investment materials. This has been found to increase further thermal expansion.

The natural starch used in the present invention include potato starch, maize starch, wheat starch, rice starch, sweet potato starch and cassaba starch, which may be used alone or in combination. Particular preference is given to potato starch. As the soluble starch, use may be made of the foregoing types of natural starch alone or in combination, which are treated with oxidizing agents such as mineral acids, sodium hypochlorite or calcium hypochlorite. However, particular preference of soluble starch is given to the natural starch treated with sodium hypochlorite.

The amount of natural starch to be added is in a range of 2 to 5 parts by weight per 100 parts by weight of a mixture of hemihydrate gypsum, quartz and/or cristobalite. In an amount below 2 parts by weight, the natural starch gives to the investment materials only insufficient thermal expansion, and has no appreciable effect upon improvements in air permeability. In an amount exceeding 5 parts by weight, on the other hand, it roughens the surface of the cast product.

The amount of the soluble starch to be added is properly in a range of 0.1 to 1.0 part by weight per 100 parts by weight of a mixture of hemihydrate gypsum, quartz and/or cristobalite. In an amount below 0.1 part by weight, it has no appreciable effects upon improvements in the reproducibility of the wax surface and prevention of a lowering of the flowability of the slurry. In an amount exceeding 1 part by weight, on the other hand, it delays the setting time of the investment material.

The investment material for dental casting according to the present invention contains as the main component a mixture of hemihydrate gypsum, quartz and/or cristobalite. Out of these, quartz and cristobalite are refractory materials, while hemihydrate gypsum acts as a binder for affording molding capacity and strength to such investment materials. As is the case with the prior art, the investment material according to the present invention may contain setting controlled agents for hemihydrate gypsum which act as setting accelerator such as inorganic acid salts (NaCl, $K_2SO_4$, etc) and alkali and finely divided dihydrate gypsum, setting retarders such as borax, salts of sodium carboxylate and colloids, lightening materials such as alumina silica or Fyrite and/or coloring agents. Even in this case, the natural starch and the soluble starch have the substantially same effects.

In what follows, the present invention will now be explained in further detail with reference to the following non-restrictive examples.

EXAMPLES 1-19

Hemihydrate gypsum, quartz, crostobalite, natural starch and soluble starch were weighed according to the proportions as specified in a table, and were mixed together in a mortar to prepare investment materials. Water was then added to 100 g of the investment materials at various proportions which were determined according to Standard Consistency Testing Method of JIS T6601 DENTAL INVESTMENT MATERIALS, followed by kneading. In this manner, cylindrical samples of 10 mm in diameter and 50 mm in length were prepared for the measurement of thermal expansion. The samples were measured on their thermal expansion with a thermal expansion measuring device. The measurement was commenced from 1 hour after the start of kneading and was completed after 3 hours therefrom, during which the samples were heated to a temperature of 700° C.

For the measurement of castability, was patterns for single crowns prepared by means of a clinical model were invested with the samples to prepare casting molds. Thereafter, with a high-frequency, centrifugal casting machine, commercially available nickel-chromium alloys (manufactured under the trade name of TIECROWN by G-C DENTAL INDUSTRIAL CORP.) to obtain cast products.

Examination was made of the fitness of the cast products to the models as well as the casting surface state and the occurrence of casting deficiencies such as misrun, cold shut, pin-hole, etc., which correlate to the reproducibility of the surface state of the wax pattern. Furthermore, examination was made of the flowability of the investment materials in a slurried state during the investing of the wax patterns for single crowns.

COMPARISON EXAMPLES 1-3

Hemihydrate gypsum, quartz and cristobalite were weighed according to the proportions as specified in the table, and were mixed together in a mortar to prepare investment materials. Thereafter, the casting molds of wax patterns for single crowns were prepared using the setting expansion (esp. the hygroscopic expansion). Testing was effected according to Examples 1 to 19. The testing results of Examples 1 to 19 and Comparison Examples 1 to 3 are shown in the table. FIG. 1 showing the thermal expansion curves obtained in Examples 3 and 5 as well as Comparison Examples 1 and 2 with temperature as abscissa and thermal expansion as ordinate.

TABLE

| | Composition (parts by weight) | | | | | | Water/Powder Ratio (W/P) | Flowability of Slurry | Thermal Expansion at 700° C. (%) | Castability | | |
|---|---|---|---|---|---|---|---|---|---|---|---|---|
| | Hemihydrate Gypsum | Quartz | Cristobalite | Natural Starch | Soluble Starch | Additive | | | | Fitness | Casting Surface | Casting Deficiencies |
| Example 1 | 20 | 80 | — | Potato Starch 2 | 0.1 | — | 0.30 | Excellent | 1.8 | Good | Excellent | Non |
| Example 2 | 25 | 75 | — | Potato Starch 3 | — | — | 0.31 | Good | 1.7 | " | Good | " |
| Example 3 | 30 | 70 | — | Potato Starch 4 | — | — | 0.31 | " | 1.8 | " | " | " |
| Example 4 | 30 | — | 70 | Potato Starch 3 | — | — | 0.31 | " | 2.1 | " | " | " |
| Example 5 | 30 | — | 70 | Potato Starch 3 | 0.5 | — | 0.30 | Excellent | 2.2 | " | Excellent | " |
| Example 6 | 40 | — | 60 | Potato Starch 4 | — | — | 0.31 | Good | 2.2 | " | Good | " |
| Example 7 | 40 | 30 | 30 | Potato Starch 5 | — | — | 0.29 | " | 1.7 | " | " | " |
| Example 8 | 45 | 20 | 35 | Potato Starch 5 | 1.0 | — | 0.26 | Excellent | 1.9 | " | Excellent | " |
| Example 9 | 35 | 65 | — | Potato Starch 3 Sweet Potato Starch 1 | — | — | 0.31 | Good | 1.7 | " | Good | " |
| Example 10 | 35 | 30 | 35 | Potato Starch 3 Sweet Potato Starch 1 Maize Starch 1 | 0.3 | — | 0.28 | Excellent | 1.7 | " | Excellent | " |
| Example 11 | 28 | 22 | 50 | Sweet Potato Starch 2 Cassaba Starch 1 | 0.7 | — | 0.29 | Excellent | 1.8 | " | Excellent | " |
| Example 12 | 22 | 78 | — | Cassaba Starch 3 Wheat Starch 1 Rice Starch 1 | — | — | 0.31 | Good | 1.9 | " | Good | " |
| Example 13 | 28 | 72 | — | Potato Starch 3 | — | NaCl 0.5 | 0.31 | " | 1.7 | " | Good | " |
| Example 14 | 27 | — | 73 | Potato Starch 3 | 0.5 | K₂SO₄ 0.2 Finely divided dihydrate gypsum 0.2 | 0.30 | Excellent | 2.2 | " | Excellent | " |
| Example 15 | 30 | — | 70 | Potato Starch 2 | — | Sodium gluconate | 0.31 | Good | 2.1 | " | Good | " |

TABLE-continued

| | Composition (parts by weight) | | | | | | Water/Powder Ratio (W/P) | Flowability of Slurry | Thermal Expansion at 700° C. (%) | Castability | | |
|---|---|---|---|---|---|---|---|---|---|---|---|---|
| | Hemihydrate Gypsum | Quartz | Cristobalite | Natural Starch | Soluble Starch | Additive | | | | Fitness | Casting Surface | Casting Deficiencies |
| Example 16 | 40 | 30 | 30 | Sweet Potato Starch 1 | — | 0.2 | 0.29 | " | 1.8 | " | " | " |
| Example 17 | 25 | — | 75 | Potato Starch 5 | 0.1 | Borate 0.3 NaCl 0.8 | 0.30 | Excellent | 2.1 | " | Excellent | " |
| Example 18 | 25 | 20 | 55 | Sweet Potato Starch 3 Wheat Starch 1 | — | Aluminum silicate 1.0 | 0.30 | Good | 1.7 | " | Good | " |
| Example 19 | 28 | — | 72 | Potato Starch 2.5 | — | Red ochre 0.1 NaCl 1.2 Gelatin 0.1 Pyrite 0.5 Chrome yellow 0.1 | 0.30 | " | 2.0 | " | " | " |
| Comparison Example 1 | 30 | 70 | — | — | — | — | 0.31 | " | 1.0 | Bad | " | Mark |
| Comparison Example 2 | 30 | — | 70 | — | — | — | 0.31 | " | 1.4 | " | " | " |
| Comparison Example 3 | 45 | 20 | 35 | — | — | — | 0.31 | " | 0.7 | " | " | " |

As evidently appreciated from the table, the investment materials of Examples 1 to 19 containing natural starch show a thermal expansion of 1.7 to 2.2% at 700° C., that is larger as compared with 0.7 to 1.4% of Comparison Examples 1 to 3. It is also confirmed that the process of thermal expansion taking place by way of natural starch in a temperature zone of 75° to 110° C., as clearly understood from the thermal expansion curves of the FIG. 1. Referring to fitness, the investment materials of Examples 1 to 19 containing natural starch and making only use of thermal expansion show good fitness, but those of Comparison Examples 1 to 3 free from natural starch show deformation of the wax patterns and bad fitness as a result of the combination of the setting expansion (esp. the hygroscopic expansion) with thermal expansion. Referring to casting deficiencies, the investment materials of Examples 1 to 19 exhibit favorable air permeability and showed no sign of any deficiency, but those of Comparative Examples 1 to 3 showed casting deficiencies such as misrun, pin-holes, etc.

The investment materials of Examples 1, 5, 8, 10, 11, 14 and 17 contain soluble starch in addition to natural starch, and so they excel in flowability in a slurried state and workability during the preparation of the cylindrical thermal expansion samples and the investing of the wax patterns for single crowns, in spite of the fact that they have a similar composition and a lower water/powder ratio, as noted from comparison with Examples 2, 3, 4, 6, 7, 9, 12, 13, 15, 16, 18 and 19, in particular, comparison of Example 4 with 5.

Furthermore, single crowns were prepared with the casting molds formed of those investment materials. Such crowns were found to have smooth casting surfaces with very faithful reproducibility of the wax patterns.

What is claimed is:

1. An investment material for dental casting, in which 2 to 5 parts by weight of natural starch are added to 100 parts by weight of a mixture of hemihydrate gypsum, quartz and/or cristobalite.

2. An investment material for dental casting, in which 2 to 5 parts by weight of natural starch and 0.1 to 1.0 part of soluble starch are added to 100 parts by weight of a mixture of hemihydrate gypsum, quartz and/or cristobalite.

* * * * *